United States Patent [19]

Hedstrand et al.

[11] Patent Number: 5,560,929
[45] Date of Patent: Oct. 1, 1996

[54] STRUCTURED COPOLYMERS AND THEIR USE AS ABSORBENTS, GELS AND CARRIERS OF METAL IONS

[75] Inventors: David M. Hedstrand; Bradley J. Helmer; Donald A. Tomalia, all of Midland, Mich.

[73] Assignee: The Dow Chemical Company, Midland, Mich.

[21] Appl. No.: 152,335

[22] Filed: Nov. 12, 1993

Related U.S. Application Data

[63] Continuation-in-part of Ser. No. 8,275, Jan. 22, 1993, abandoned, which is a continuation-in-part of Ser. No. 654,851, Feb. 13, 1991, Pat. No. 5,338,532, which is a continuation-in-part of Ser. No. 386,049, Jul. 26, 1989, abandoned, which is a continuation-in-part of Ser. No. 87,266, Aug. 18, 1987, abandoned, which is a continuation-in-part of Ser. No. 897,455, Aug. 18, 1986, abandoned.

[51] Int. Cl.$^6$ .................................................. A61K 31/78
[52] U.S. Cl. .................. 424/486; 424/78.08; 424/78.1; 424/78.17; 424/78.18; 424/78.26; 424/400; 424/487; 521/28; 521/30; 525/539
[58] Field of Search .................................. 424/486, 400, 424/487, 78.26, 78.08, 78.1, 78.17, 78.18; 521/28, 30; 525/539

[56] References Cited

U.S. PATENT DOCUMENTS

| | | |
|---|---|---|
| 3,200,106 | 8/1965 | Dickson et al. . |
| 3,445,441 | 5/1969 | Rushton . |
| 3,514,250 | 5/1970 | Rushton . |
| 3,528,928 | 9/1970 | Rushton . |
| 3,578,643 | 5/1971 | Wood et al. . |
| 3,580,891 | 5/1971 | Rainer . |
| 3,773,739 | 10/1973 | Bonvicini et al. . |
| 4,036,808 | 7/1977 | Rembaum et al. . |
| 4,102,827 | 7/1978 | Rembaum et al. . |
| 4,141,847 | 2/1979 | Kivosky . |
| 4,289,872 | 9/1981 | Denkwalter et al. . |
| 4,315,087 | 2/1982 | Redmore et al. . |
| 4,360,646 | 11/1982 | Denkwalter et al. . |
| 4,410,688 | 10/1983 | Denkwalter et al. . |
| 4,435,548 | 3/1984 | Tomalia et al. . |
| 4,472,509 | 9/1984 | Ganson et al. . |
| 4,507,466 | 3/1985 | Tomalia et al. . |
| 4,558,120 | 12/1985 | Tomalia et al. . |
| 4,568,737 | 2/1986 | Tomalia et al. . |
| 4,587,329 | 5/1986 | Tomalia et al. . |
| 4,606,907 | 8/1986 | Simon et al. . |
| 4,631,337 | 12/1986 | Tomalia et al. . |
| 4,634,586 | 1/1987 | Goodwin et al. . |
| 4,675,173 | 6/1987 | Widdor . |
| 4,694,064 | 9/1987 | Tomalia et al. . |
| 4,713,975 | 12/1987 | Tomalia et al. . |
| 4,737,550 | 4/1988 | Tomalia . |
| 4,824,659 | 4/1989 | Hawthorne . |
| 4,855,403 | 8/1989 | Meschke et al. . |
| 4,857,218 | 8/1989 | Meschke et al. . |
| 4,857,599 | 8/1989 | Tomalia et al. . |
| 4,863,717 | 9/1989 | Keans . |
| 4,871,779 | 10/1989 | Killat et al. . |
| 4,916,246 | 4/1990 | Felder et al. . |
| 4,938,885 | 7/1990 | Migdal . |
| 4,946,824 | 8/1990 | Meschke et al. . |
| 4,980,148 | 12/1990 | Dean . |
| 5,021,236 | 6/1991 | Gries et al. . |
| 5,039,512 | 8/1991 | Kraft et al. . |
| 5,041,516 | 8/1991 | Frechet et al. . |
| 5,098,475 | 3/1992 | Winnik et al. . |
| 5,120,361 | 6/1992 | Winnik et al. . |
| 5,154,853 | 10/1992 | Newkombe et al. . |
| 5,175,270 | 12/1992 | Nilsen et al. . |

FOREIGN PATENT DOCUMENTS

| | | |
|---|---|---|
| 560604 | 7/1987 | Australia . |
| 3827589 | 2/1990 | Australia . |
| 0115771 | 8/1984 | European Pat. Off. . |
| 0271180 | 6/1988 | European Pat. Off. . |
| 0430863 | 11/1990 | European Pat. Off. . |
| 0469520 | 2/1992 | European Pat. Off. . |
| 0481526 | 4/1992 | European Pat. Off. . |
| 206742 | 8/1987 | New Zealand . |
| 840128 | 8/1985 | South Africa . |
| 8402705 | 7/1984 | WIPO . |
| 9012050 | 10/1990 | WIPO . |
| 9011778 | 10/1990 | WIPO . |
| 9314147 | 7/1993 | WIPO . |

OTHER PUBLICATIONS

J. Macromol. Science–Chemistry., A17(4) pp. 689–703 (1982).
J. Nucl. Med., 27, pp. 829–833 (1986), Anderson et al.
Proc. Nat'l Acad. Sci. (U.S.A.), 85, pp. 5409–5413 (1988), Tam.
Journal of Molecular Catalysis, 32, pp. 149–158 (1985), Savinova et al.
Journal of Molecular Catalysis, 32, pp. 159–175 (1985), Savinova et al.
Bioconjugate Chemistry, 1, pp. 305–308 (1990), Roberts et al.
Angew Chem., Int. Ed. Engl., 29, pp. 138–175 (1990), Tomalis et al.
Polymer Journal, 17(1), pp. 117–132 (Jan. 1985), Tomalia et al.
Macrocolecules, 19(9), pp. 2466–2468, Tomalia et al.
Biochem. Biophys, Acta, 883, (1986), Manabe et al.
Byull, Eksp, Biol. Med. (BEBMAE), 102(7), pp. 63–65 (1986), Torchilin et al.

(List continued on next page.)

Primary Examiner—Thurman K. Page
Attorney, Agent, or Firm—Karen L. Kimble

[57] ABSTRACT

Dense star polymers or dendrimers having a highly branched interior structure capable of associating or chelating with metal ions are modified by capping with a hydrophobic group capable of providing a hydrophobic outer shell. The modified dendrimers are useful for dispersing metal ions in a non-aqueous polymer matrix. Also dense star polymers or dendrimers having a highly branched hydrophilic interior structure are modified by capping with a hydrophobic group capable of providing a hydrophobic outer shell, which modified polymers are useful as gels and surfactants.

23 Claims, No Drawings

OTHER PUBLICATIONS

Nature, 225, pp. 387–488 (Jun. 5, 1975), Rowland et al.
Proceedings Nat'l Acad. Sci. (U.S.A.), 83, pp. 4277–4281 (1986), Curtet et al.
*Polymer Journal*, 24, (6), pp. 573–581 (1992).
J. Chem. Soc. Chem. Commun., 1992, pp. 608–610.
*The Chemical society of Japan. Chemistry Letters*, pp. 959–962, (1992).
*Angew. Chem. Int. Ed. Engl.*, 31, (12), (1992).
*J. Org. Chem.*, 52, pp. 5305–5312, (1987).
*J. Am. Chem. Soc.*, 109, pp. 1601–1603, (1987).
*Macromolecules*, 20, pp. 1164–1167, (1987).
*Angew. Chem. Int. Ed. Engl.*, 31, (1), pp. 1493–1495, (1992).
*J. Am. Chem. Soc*, 111, pp. 2339–2341, (1989).
*J. Am. Chem. Soc.*, 112, pp. 4592–4593, (1990).
*J. Org. Chem.*, 50, pp. 2003–2004, (1985).
*J. Am. Chem. Soc.*, 112, pp. 8458–8465, (1990).
*J. Chem. Soc. Chem. Commun.*, (8), 1992.
*Acc. Chem. Res.*, 24, pp. 332–340, (1991).
*J. Am. Chem. Soc.*, 113, pp. 7335–7342, 1991.
*Bioconjugate Chem.*, 1, (5), 1990.
Poly. Prep. 32, (31), pp. 602–603, (1991).
*J. Org. Chem.*, 57, p. 435, (1992).
*Progress in Neutron Capture Therapy for Cancer*, Plenum Press, New York, 1992, pp. 265–268.
*Macromolecules*, 25, pp. 910–912, (1990).
*Angew. Chem. Int. Ed. Engl.*, 30, pp. 1177–1180, (1991).
Condensed Chemical Dictionary, 7th ed., Reinhold Publishing Co., N.Y., p. 893 (1966).
Telechelic Polymers: Synthesis and Applications, ed. Eric Goetherls, CRC Press (1989).
Domain Structure and Properties of Block and Graft Copolymers and Polymer Blends, Kyoto University (1979).
Advanced Organic Chemistry, 3D Ed., (1985) Jerry march.
Monabe et al Biochim. Biophysica Acta (1986) 460–467 vol. 883.
Chem. Abstracts 105: 131708w.

STRUCTURED COPOLYMERS AND THEIR USE AS ABSORBENTS, GELS AND CARRIERS OF METAL IONS

STATEMENT OF FEDERALLY SPONSORED RESEARCH

This invention was made with U.S. Government support under subcontract, number 9751405, between The University of California and The Dow Chemical Company. The University of California held the primary contract, number W-7405-ENG-48, which was awarded to The University of California by the Department of Energy. The U.S. Government has certain rights in this invention with regard to dense star polymers which have metal ions present and matrix polymers which have metal ions present. Other aspects of this present invention are not subject to U.S. Governmental rights.

CROSS REFERENCE TO RELATED APPLICATIONS

This application is a continuation-in-part of our application Ser. No. 008,275, filed Jan. 22, 1993 now abandoned, which is a continuation-in-part of Ser. No. 654,851, filed Feb. 13, 1991 now U.S. Pat. No. 5,338,532, which is a continuation-in-part application of Ser. No. 386,049, filed Jul. 26, 1989, now abandoned, which is a continuation-in-part application of Ser. No. 087,266, filed Aug. 18, 1987, now abandoned, which is a continuation-in-part of Ser. No. 897,455, filed Aug. 18, 1986, now abandoned.

FIELD OF THE INVENTION

This invention concerns structured copolymers and their use as absorbents, gels and carriers of metal ions. Unique polymeric reagents are used which are capable of extracting metal ions from aqueous solutions into non-aqueous solutions containing structured copolymers. In addition, these structured copolymers containing the metals are capable of being dispersed into another polymeric matrix. More particularly, the present invention concerns a novel class of dense star polymers having a highly branched interior structure comprised of monomeric units having the ability to associate or chelate with metal ions and an exterior comprised of a different monomeric unit having the ability to provide a hydrophobic outer shell.

Additionally, the dense star polymers, having a highly branched interior structure comprised of monomeric units that are hydrophilic and an exterior comprised of different monomeric units having the ability to provide a hydrophobic outer shell, display a unique physical feature of forming a homogeneous gel.

BACKGROUND OF THE INVENTION

The ability to disperse metal ions in polymer matrices, particularly those from which foams are produced (see our U.S. Patent Applications Ser. No. 008,276, filed Jan. 22, 1993 and now abandoned, entitled "Process for the Preparation of Blends and Their Use in Small Cell Foams" and Ser. No. 08/148,440, filed Nov. 8, 1993and now U.S. Pat. No. 5,386,617, entitled "Small Cell Foams and Blends and a Process for Their Preparation") is often fraught with difficulty. Dispersions of metals in polymer matrices have typically been formed using salts, such as metal oleate salts, combined with specific combinations of monomers, but there are problems with this approach. In order to maximize the solubility of the salt, modifications of the polymer matrix are required that change the melt rheology of the matrix and affect its foaming characteristics. In addition, the presence of certain metal oleates, such as copper oleate, in the monomer often inhibit polymerization so that only low molecular weight viscous liquids are obtained. This approach obviously introduces significant variables that must be controlled in order to obtain the desired product. As a result, the complexity of the problem and any potential solutions are vastly increased. Therefore, new methods of dispersing metals in water-immiscible phases in general and in polymer matrices in particular would be most useful.

The formation of a gel in a two phase system (aqueous/organic) has use in an oil/water emulsion system for use as a surfactant. Some known problems arise with regard to holding large quantities of the organic phase within the continuous aqueous phase. As a result, the ability to use a gel for this purpose would be useful.

In recent years, polymers referred to as dense star polymers or dendrimers or as STARBURST™ (a trademark of Dendritech Inc.) polymers have been developed. Dense star polymers or dendrimers exhibit molecular architecture characterized by regular dendritic branching with radial symmetry. These radially symmetrical molecules are referred to as possessing "starburst topology". These polymers are made in a manner which can provide concentric dendritic tiers around an initiator core. The starburst topology is achieved by the ordered assembly of repeating units, usually organic groups, in concentric, dendritic tiers around an initiator core; this is accomplished by introducing multiplicity and self-replication (within each tier) in a geometrically progressive fashion through a number of molecular generations. The resulting highly functionalized molecules have been termed "dendrimers" in deference to their branched (tree-like) structure as well as their oligomeric nature. Thus, the terms "dense star oligomer" and "dense star dendrimer" are encompassed within the term "dense star polymer". Also topological polymers, with size and shape controlled domains, are dense star dendrimers that are covalently bridged through their reactive terminal groups, which are referred to as "dense star bridged dendrimers." The term "dense star bridged dendrimer" is also encompassed within the term "dense star polymer" and "dense star polymer".

These dense star polymers have been previously described as a solvent soluble, radially symmetrical dense star polymer wherein the dense star polymer has at least one core branch emanating from a core, said branch having at least one terminal group provided that (1) the ratio of terminal groups to the core branches is two or greater, (2) the density of terminal groups per unit volume in the polymer is at least 1.5 times that of an extended conventional star polymer having similar core and monomeric moieties and a comparable molecular weight and number of core branches, each of such branches of the extended conventional star polymer bearing only one terminal group, and (3) the dense star polymer has a molecular volume that is no more than about 60 to 80 percent of the molecular volume of said extended conventional star polymer as determined by dimensional studies using scaled Corey-Pauling molecular models, and has regular dendritic branching. (See, for example, the descriptions of dense star polymers in U.S. Pat. Nos. 4,507,466; 4,558,120; 4,568,737; 4,587,329; and 4,694,064; and European Patent Application Publication No. 0 271 180, the disclosures of which are hereby incorporated by reference.) It has been previously found that the size, shape and properties of these dense star polymers can be molecularly tailored to meet specialized end uses (e.g., European Patent Application Publication No. 0 271 180, the disclosure of which is hereby incorporated by reference). Among such specialized end uses, European Patent Application Publication No. 0 271 180, the disclosure of which is hereby incorporated by reference, teaches the use of dense star polymers as carriers for agricultural, pharmaceutical or other materials including metal ions, such as alkali and alkaline-earth metals and radionuclides generated from actinides or lanthanides or other similar transition metals. Such dense star polymer conjugates are particularly useful in delivering carried materials in biological systems. However, nowhere is the use of such structured dense star dendrimers as absorbents, gels and carriers of metal ions taught or suggested.

SUMMARY OF THE INVENTION

It has now been found that certain modified or structured dense star polymers are particularly effective in extracting metal ions from aqueous solutions into non-aqueous solutions containing these structured copolymers. In addition, these structured copolymers containing the metals are capable of being dispersed into another polymeric matrix. The present invention concerns these modified dense star polymers or dendrimers having a highly branched interior structure comprised of monomeric units having associated or chelated at least one metal ion and an exterior structure comprised of a different monomeric unit providing a hydrophobic outer shell. Similar hydrophobic dense star polymers and dendrimers are also included which lack the presence of a metal ion.

The present invention includes a polymer blend comprising a modified dense star polymer associated with a metal ion and a polisher matrix.

Additionally, the use of the present modified dense star polymer or dendrimer in the formation of a gel in a two phase system (aqueous/organic) has use in an oil/water emulsion system for use as a surfactant.

DETAILED DESCRIPTION OF THE INVENTION

The dense star polymers which comprise the highly branched interior structure of the modified dense star polymers of the present invention must have an affinity to associate, complex or chelate with metal ions. Such affinities are usually achieved by incorporating a plurality of oxygen or nitrogen atoms, which readily complex with metal ions, within the highly branched structure of the dense star polymer which serves as the core. Such dendrimers are known compounds and can be prepared according to the procedures described, for example, in U.S. Pat. Nos. 4,568, 737 and 4,587,329 and in European Patent Application Publication 0 271 180 and WO 93/14147, the disclosures of which are hereby incorporated by reference Preferred dense star polymers for use in the present invention are amine-terminated poly(amidoamine) dendrimers, hydroxy-terminated poly(ether) dendrimers, amine-terminated poly(ethyleneimine) dendrimers, and amine-terminated poly(propyleneimine) dendrimers. Most preferable are those poly(amidoamine), poly(ether), poly(ethyleneimine) and poly(propyleneimine) dendrimers of from 2 to 12 generations, i.e., in which the monomeric unit is repeated from 6 to 15,000 times.

The exterior structure of the modified dense star polymers of the present invention which imparts the hydrophobic nature to the outer shell is comprised of hydrophobic groups.

The term "hydrophobic groups" means groups lacking an affinity for, repelling, or failing to adsorb or absorb water ["Dictionary of Scientific and Technical Terms", Ed. Sybil P. Parker, 4th ed . (1989)]. The hydrophobic groups on the surface of the dense star polymer must be soluble in, miscible in or compatible with the matrix polymer used to make the blends, and the interior of the hydrophobic dense star polymer must be substantially less soluble in, miscible in or compatible with the matrix polymer.

"Matrix polymers" means polymers that are soluble in, miscible in or compatible with the hydrophobic groups on the surface of the hydrophobic dense star polymer. Examples of suitable matrix polymers used in this invention are thermoplastic polymers, such as polyethylene, polypropylene, polystyrene, polyacrylate, polymethyl methacrylate, polyisobutylene, and polymethylpentene.

Such hydrophobic groups usually include a reactive functional group such as an acid chloride, ester, carboxylic acid, halide (i.e., chloride or bromide), acrylate, or epoxy ether. Preferred hydrophobic groups are hydrocarbon groups of from 4 to 40 carbon atoms inclusive, preferably from 4 to 24. These hydrophobic groups may also contain oxygen, nitrogen or sulfur atoms, e.g. epoxy, hydroxy, ester or ether groups. However, all substituent groups must be sterically compatible with each other.

The term "sterically compatible" is employed to designate substituent groups which are not affected by steric hindrance as this term is defined in "The Condensed Chemical Dictionary" 7th edition, Reinhold Publishing Co., New York page 893 (1966) which definition is as follows: "steric hindrance. A characteristic of molecular structure in which the molecules have a spatial arrangement of their atoms such that a given reaction with another molecule is prevented or retarded in rate." Sterically compatible may be further defined as reacting compounds having substituents whose physical bulk does not require confinement within volumes insufficient for the exercise of their normal behavior as discussed in *Organic Chemistry* of D. J. Cram and G. Hammond, 2nd edition, McGraw-Hill Book Company, New York, page 215 (1964).

Such hydrocarbon groups include linear alkyl groups having from 4 to 40 carbon atoms optionally substituted independently with hydroxy, with carboxyl, with $C_1$–$C_{10}$ alkyl, with $C_1$–$C_{10}$ alkoxy, with $C_1$–$C_{10}$ alkoxycarbonyl, with phenyl or phenyl substituted with from 1 to 5 groups of $C_1$–$C_5$ alkyl or $C_1$–$C_5$ alkoxy groups, or with phenoxy or phenoxy substituted with $C_1$–$C_5$ alkyl or $C_1$–$C_5$ alkoxy groups. Examples of such hydrocarbon groups are hexyl, octadecyl, ethylhexyl, tolyldecyl group, anisyldodecyl group, 3-phenoxy-2-hydroxy- 1-propyl, (4-methyl)phenoxy-2-hydroxy-1-propyl, (4-methoxy)phenoxy-2-hydroxy-1-propyl, telechelic polymers (which are polymers having a single functional group at their end as described in *Telechelic Polymers:Synthesis and Applicationed*, Eric Goetheis, CRC Press 1989), 2-hydroxyalkyl moieties formed from the opening of epoxy moieties, and alkylation of the hydroxy groups from the 2-hydroxyalkyl moieties to provide the alkoxy groups.

The modified dendrimers of the present invention are prepared by capping the dense star polymers which comprise the highly branched interior structure with a hydrophobic tail. The capping reaction may be performed in any conventional manner suitable for the reactive groups present. Some examples of these reactions can be found in *Advanced Organic Chemistry*, 3rd ed., John Wiley & Sons, New York (1985), by Jerry March and U.S. Pat. No. 4,558, 120 at column 12.

By way of example, this can be accomplished by reacting the amine-terminated or hydroxy-terminated dendrimers which serve as the interior structure with an appropriate hydrocarbon chloride or bromide, or ($C_6$–$C_{14}$ aryl)$C_1$–$C_{11}$alkyl chloride or bromide, or with an appropriate α,β-epoxide. Reactions with either the halides or epoxides are preferably conducted by contacting the amine-terminated or hydroxy-terminated substrates with at least one equivalent of halide or epoxide for each available terminal amine or hydroxy group in the presence of an inert solvent under basic or neutral conditions. The reaction can be conducted under temperatures ranging from 20° C. to about 150° C. Preferred hydrocarbon halides are primary alkyl chlorides and bromides which, when subjected to conditions favoring bimolecular nucleophilic substitution reactions, provide amines and ethers capped with primary hydrocarbon tails. Preferred epoxides are those derived from the epoxidation of terminal olefins which, when subjected to ring opening under basic or neutral conditions, provide predominantly amines and ethers capped with primary hydrocarbon tails substituted with hydroxy groups in the β-position. Among the most preferred capping materials are, for example, iso-octyl bromide, cetylbromide, lauryl bromide, glycidyl phenyl ether, glycidyl iso-propyl ether, glycidyl t-butyl ether, glycidyl 1-naphthyl ether, glycidyl 4-methoxyphenyl ether, glycidyl 2-methylphenyl ether, 1,2-epoxydecane, 1,2-epoxyoctadecane, 4,4-diphenyl-1-butene oxide and 11,11-diphenyl-1-undecene oxide.

As an alternative to mixing the hydrophobic modified dense star polymer or dendrimer with a continuous polymeric matrix in a suitable solvent, one may admix the appropriate hydrophobic modified dense star polymer or dendrimer directly with the polymer phase utilizing known melt blending processes, i.e. blending in a Brabender mixer.

By modifying the composition of the exterior structure, the overall solubility of the dendrimer can be significantly tailored to fit a specific application. In addition, when advanced through sufficient generations, these dendrimers exhibit "dense packing" where the surface of the dendrimer contains sufficient terminal moieties such that the dendrimer surface becomes sterically congested and encloses void spaces within the interior of the dendrimer. This congestion can provide a molecular level barrier which can be used to control diffusion of materials into or out of the interior of the dendrimer.

The selection of the hydrophobic groups necessary to effect the homogeneous dispersion of the modified dense star polymers within a given or desired polymer matrix is within the capability of one skilled in the art. This selection of hydrophobic groups for a given polymer matrix can be understood by analogy to block copolymer blend:s.

The thermodynamics of blends of high molecular weight materials do not have large enough entropy of mixing contributions to stabilize the solutions, unless the polymer components are very close in their surface energy. The stability of the dispersion of one polymer within another is dominated by the interfacial energies between the microscopic domains of the two components. Thus, a blend of the two homopolymers will tend to separate into two distinct phases in order to minimize the interfacial area and total energy of the system.

It is known in the art that a stable blend can be prepared if one of the components is a block copolymer composed of segments with much different solubility parameters. See, for example, *Domain Structure and Properties of Block and Graft Copolymers and Polymer Blends*, pub. Kyoto University (1979), by the Research Staff of Polymer Mechanics Laboratory at the Department of Polymer Chemistry, Faculty of Engineering, Kyoto University. In this case, there is a considerable interfacial energy between the segments of the copolymer. This is relieved when the segments of the copolymer are separated or found to be compatible with another component of the blend, preferably at least one other component. With appropriate choices of homopolymer and copolymer compositions, this high internal energy within the copolymer is greater than the interfacial energy between the two polymers one is attempting to compatibilize and as a consequence the blend is more stable than the two distinct phases.

While not wishing to be bound by theory, a similar situation is believed to exist in the blends employed in the present invention. Experimental and theoretical studies of the dense star polymers suggest that many of the end groups of the molecules are folded back into the interior of the molecule in order to fill space efficiently. This implies that there may be considerable interaction of the surface modifying groups with the interior groups of the molecule when the material is not blended. This high energy interaction within the dendrimer s relieved when the dense star polymer is used as a component in the blends of the present invention. The best choice of compositions to optimize the stability of the blend maximizes the differences between interior and end groups within the dense star polymer and minimizes the interfacial energy between the matrix polymer and the dense star polymer. Thus, the aromatic derivatives as modifications are superior to the aliphatic hydrocarbon derivatives as modifications in blends with polystyrene. On the other hand, aliphatic surface groups on the dendrimer may be superior as modification for compatibilizing dendrimers in acrylate/methacrylate type systems.

Minimization of interfacial energy is expected to minimize the interface area between the various microphases. This would be achieved by placing all of the copolymeric end groups in a spherical shell, or a portion of a spherical shell on the surface of the macromolecular particle. Thus, controlled microphase separation is achieved with groups that are not immediately connected to each other. When the multiplicity of end groups is sufficient to form a continuous spherical shell, this shell serves to form a barrier between the interior of the dendrimer macromolecule and the matrix polymer in which it is dispersed.

While not wishing to be bound by theory, it is believed that the advantageous results of the present invention in the selection of the hydrophobic groups is the result of an energetically favorable balance of the interfacial energies between the components o the blend. This favorable balance is best exemplified when the volume ratio (v/v) of the exterior groups to the highly branched interior structure is about 1:10 to 10:1, preferably 1:5 to 5:1, more preferably about 1:1.

The metal ions that are extracted by the modified dense star polymers of this invention must be capable of association with the highly branched interior structure of the modified dense star polymer. Suitable examples of such metal ions are salts of: transition metals of Groups VIA (Cr), VIIA (Mn), VIIIA (Fe), IB (Cu), and IIB (Zn); alkali metals of Group IA (Li); alkaline earth metals of Group IIA (Be); lanthanides metals of Group IIIA (La); Y; Gel; Sn; and Pb.

The term "associated with" includes attached to or linked to or encapsulated within the interior of the modified dense star polymer by means of covalent bonding, hydrogen bonding, adsorption, absorption, chelation, metallic bonding, van der Waals forces, ionic bonding, coulombic forces, hydrophobic or hydrophilic forces, or any combination thereof.

The ability of these dense star polymers to extract metals from aqueous solution provides a wide range of utilities, not limited to water purification or precious metals recovery, where a small volume of organic solution can be agitated with a large volume of aqueous phase to, in effect, remove the metals from the water and concentrate them in a more processable and/or recoverable medium. This ability also simplifies the preparation of the metal loaded dense star polymers for subsequent dispersion in a polymer matrix. Metals dispersed in polymer matrices can add electromagnetic radiation absorption properties to the polymeric material, making them useful for radiation shielding or as a microwave heatable material.

The use of the dense star dendrimers of this invention as surfactants and as gels can be illustrated by their physical characteristics. The acylated dense star dendrimers are usually insoluble in toluene and water, but demonstrate a unique physical feature when dispersed in a two phase aqueous/organic medium. The result is a homogeneous opaque white gel. This gel forms as the amide is produced in the two phase reaction (<1 minute) and becomes thick and non-flowing. Filtration of this gel (5 wt % product in 1:1, $H_2O$:toluene) removes some of the solvent and gives a stiff moist solid (10–20 wt % product). Rotary evaporation gives a powder which still contains 50% solvents, and drying in a vacuum oven produces dried material.

The gel can also be diluted beyond the original 5 wt % in $H_2O$/toluene. Dilution as low as 1% gives a thickened white gel. This thickening is broken down by agitation, but reforms in 30 min to 1 hour. Further dilution with water (i.e., mixed in a blender) gives a milky white liquid, while addition of toluene merely results in separation of a clear toluene layer. Hence the capacity for water (in a water/toluene mixture) is unlimited, while that capacity for toluene (in $H_2O$/toluene) is limited to a 25–50 fold weight excess of toluene over dendrimer. When toluene is evaporated from the milky white dilutions in water, the dendrimer precipitates out and leaves a clear aqueous phase.

These results imply that there is an oil/water emulsion with dense star dendrimer acting as surfactant and capable of holding large quantities of toluene within the aqueous continuous phase. Furthermore, the dense star dendrimers become insoluble in water unless large amounts of toluene are present to reduce self-association and disperse the dense star dendrimers. This is also seen at high concentrations (>10 wt %) of dense star dendrimer in $H_2O$/toluene where the capacity for water ($R=C_5<Ph<C_7<C_9$) is limited to approximately the volume of toluene present.

While not wishing to be bound by theory, it is believed that the thickening phenomenon results due to a three-dimensional hydrophobic network corrected by domains of toluene and held in a continuous phase of water. This hydrophobic association is also seen when small amounts of dense star dendrimer are dissolved in aqueous solutions of a nonionic surfactant, $C_8H_{17}O(CH_2CH_2O)_5H$. As the cloudy solution is heated, the surfactant loses its waters of solvation and hydrophobic association takes over to give a flocculent precipitate.

Due to the lack of solubility of the dense star dendrimers in toluene and in water, the dried product cannot be adequately dispersed in $H_2O$/toluene to form the creamy gel. Thus the gel has only been generated during the synthesis of the product, or by precipitation from acid or methanol when possible.

The hydrophobic modified dense star dendrimer and dense star polymer of this invention begins to resemble an inverted micelle wherein a hydrophilic interior is encased by a hydrophobic exterior. Furthermore, the molecular dimensions of the higher generation dendrimer (i.e. Gen=3 and higher) are very similar to those observed for micelles. While the two systems share the features of being compartmentalized and highly organized on the molecular level, they differ markedly in their dynamic behavior. Micelles break up and reform very rapidly; whereas the fixed micelle provided by the dense star dendrimer of this invention has long term stability.

The following preparative examples are illustrative of the modified dense star polymers of the present invention, which are intended to be purely exemplary of the present invention.

EXAMPLE 1

Glycidyl Phenyl Ether Derivative of Tenth Generation Polyamidoamine Dense Star Polymer A mixture of 0.65 grams (g) of generation 10 dense star polymer derived from ammonia, methyl acrylate and ethylene diamine and 0.77 g of glycidyl phenyl ether were stirred in 150 milliliters (mL) of ethanol at reflux for 2 days After cooling the mixture to 0° C., the product (1.0 g) was isolated as a white foam by filtration and characterized by:

$^{13}C$ NMR ($CDCl_3$), TMS as internal standard ppm 173.2, 159.3, 129.5, 121.2, 114.2, 64–72 (br), 48–60 (br), 32–40 (br).

The ability to extract metals from aqueous solutions is part of the present invention. The present invention concerns a process for extracting these metal ions from aqueous solutions by intimately contacting the aqueous solution containing metal ions with a solution of a modified dense star polymer, having a highly branched interior structure comprised of monomeric units having the ability to associate or chelate with metal ions and an exterior structure comprised of a different monomeric unit having the ability to provide a hydrophobic outer shell, in a water-immiscible solvent, and separating the organic phase from the aqueous solution. The modified dense star polymer containing the metal ions is then blended with another polymer to disperse the metal ions into the continuous phase matrix.

The following example is illustrative of the preparation of the modified dense star polymer containing the metal ions.

EXAMPLE 2

Extraction of Copper Ion from an Aqueous Solution by Treatment With Glycidyl Phenyl Ether Modified Tenth Generation Polyamidoamine Dense Star Polymer The modified dendrimer of Example 1 (0.6 g) was dissolved in chloroform. A solution of 0.12 g of copper sulfate in 10 mL of water was added and the mixture stirred at room temperature, overnight. The layers were separated and the aqueous layer extracted with chloroform. The combined chloroform solutions were dried with sodium sulfate and filtered. Distillation of the solvent in vacuo gave 0.6 g of blue powder.

Non-polar polymeric matrices in which metal ions have been dispersed have been found to be useful for manufacturing articles for shielding electromagnetic radiation. The present invention concerns a process for dispersing a modified dense star polymer containing metal ions into a non-polar polymer matrix which is characterized by:

(a) intimately contacting the aqueous solution containing metal ions with a solution of a modified dense star polymer, having a highly branched interior structure comprised of monomeric units having the ability to associate or chelate with metal ions and an exterior structure comprised of a different monomeric unit having the ability to provide a hydrophobic outer shell, once introduced into the water-immiscible solvent, (b) (i) optionally separating the organic phase which is usually soluble or miscible with the desired polymer matrix or the monomeric precursor to the polymeric matrix from the aqueous solution, and (ii) intermixing the modified dense star polymer carrying the associated metal ion with the non-polar media either before or after removal of the water-immiscible extraction solvent, and (c) polymerizing the mixture from step (c) when the non-polar media is a monomer.

This method is particularly useful for dispersing metal ions in non-polar polymer matrices. In such cases, after dispersing the modified dense star polymer carrying the metal ions into a suitable monomer, the mixture is subsequently polymerized (Step d).

The following example is illustrative of the dispersion process.

EXAMPLE 3

Dispersion of Copper Ion into Polystyrene Using Glycidyl Phenyl Ether Modified Tenth Generation Polyamidoamine Dense Star Polymer The copper-containing modified dendrimer of Example 2 was added to 20 g of styrene and the mixture was sonicated intermittently (total time 10 hr) over 4 days to give a homogeneous solution. Azobisisobutyronitrile (0.15 g) was added and the mixture heated in an oil bath at 100° C. for 16 hr. The resultant polymer was a dark transparent blue, except for a small portion on the bottom of the bottle that was a darker opaque blue.

EXAMPLE 4

Blend of Modified PAMAM Dendrimers with Poly(methyl methacrylate)

A: t-Butyl Glycidyl Ether Modification

To a solution of 0.5 g of generation 7 PAMAM dendrimer was added 0.56 g of t-butyl glycidyl ether (TBGE). The solution was agitated on an orbital mixer for 6 days, then the solvent and excess TBGE were removed by distillation in vacuo, giving 1.0 g of hydrophobic dendrimer which is characterized by:

$^{13}C$ NMR (CDCl$_3$), TMS as internal standard ppm 173.0, 27.6, broad peaks 65, 64, 36, 34.

The TBGE hydrophobic dense star polymer described above (0.3 g) was dissolved in 60 g of methyl methacrylate. To this; solution was added 0.4 g of azobisisobutyronitrile and the resulting solution was heated at 60° C. for 16 hrs. The resulting polymer was ground and compression molded to give transparent plaques.

B: Epoxyoctane Modification

To a solution of 0.5 g of generation 7 PAMAM dendrimer was added 0.57 g of epoxyoctane. The solution was agitated on an orbital mixer for 6 days, then the solvent and excess epoxyoctane were removed by distillation in vacuo, giving 0.8 g of hydrophobic dendrimer which is chatracterized by:

$^{13}C$ NMR (CDCl$_3$), TMS as internal standard ppm 173.0, 32.0, 29.5,, 25.8, 22.6, 14.1 broad peaks 70, 69, 64, 62, 56, 50, 38, 35.

The epoxyoctane hydrophobic dense star polymer described above (0.3 g) was dissolved in 60 g of methyl methacrylate. To this solution was added 0.4 g of azobisisobutyronitrile and the resulting solution was heated at 60° C. for 16 hrs. The resulting polymer was ground and compression molded to give transparent plaques.

EXAMPLE 5

Derivatives of 1st Generation Dense Star Dendrimer from NH$_3$ (1.0G/NH$_3$)

A:             1.0             G/NH$_3$-Acetyl; N(CH$_2$CH$_2$CONHCH$_2$CH$_2$NHCOCH$_3$)$_3$ A dense star dendrimer of generation 1 (1.0 G) from an ammonia core [N(CH$_2$CH$_2$CONHCH$_2$CH$_2$NH$_2$)$_3$], 7.50 g (62.7 meq), was dissolved in 40 mL of water and placed in a mechanically stirred 3-neck round bottom flask with 80 mL toluene. This mixture was stirred and cooled in an ice bath, and to it was added dropwise 4.7 mL (65.8 meq) acetyl chloride in 20 mL toluene. Once addition had begun, 28 mL (69.2 meq) of 10% NaOH was added.

When addition was complete, the ice bath was removed and the mixture was stirred for an additional 30 minutes (mins). The solution was then evaporated and the resulting oil was dissolved in ethanol and filtered to remove NaCl. This solution was then evaporated to give 8.6 g (85%) of the product as an oily white solid. The product was relatively insoluble in diethyl ether and toluene, but fairly soluble in water and methanol.

$^1$H NMR (D$_2$O) δ3.9 (12H, H-3,4), 3.4 (6H, H-1), 3.2 (6H, H-2), 2.7 (9H, CH$_3$). % substitution (NMR)=90%.

Designation of protons; used for NMR tabulation is as follows for all parts of Example 5:

B:             1.0             G/NH$_3$-Trimethylacetyl; N[CH$_2$CH$_2$CONHCH$_2$CH$_2$NHCO-t-C(CH$_3$)$_3$]$_3$ The first generation dendrimer from Part A, 7.5 g (63 meq), was reacted with trimethylacetyl chloride (8.1 mL, 65 mmole) as described for Part A above. The reaction was neutralized with 10% NaOH (28 mL, 70 mmole), then stirred for two hours and worked up as described for Part A above.

Evaporation of the ethanol solution and drying in a vacuum oven gave 12.3 g (96%) of the product as a white solid, mp 92°–96° C. The product was relatively insoluble in diethyl ether and toluene, but fairly soluble in water and methanol.

IR(KBr) 300, 2930, 2890, 1640, 1540, 1450 cm$^{-1}$.

$^1$H-NMR (d6-DMSO) δ3.2 (12H, H-3,4), 2.6 (12H, H-1, 2) 1.1 (27H, t-Bu); % substitution (NMR)=97%.

| Anal. $C_{30}H_{57}N_7O_6$ | | | |
|---|---|---|---|
| | C | H | N |
| calcd. | 58.9 | 9.4 | 16.0 |
| found | 56.4 | 9.1 | 14.9 |

(may contain a few percent NaCl).

C: 1.0 G/NH$_3$-Benzoyl; N[CH$_2$CH$_2$CONHCH$_2$CH$_2$NHCO—(C$_6$H$_5$)]$_3$

The first generation dendrimer from Part A, 6.8 g (57 meq), was dissolved in 40 mL of water and stirred with 50 mL of toluene at 0° C. Benzoyl chloride (6.9 mL, 59 meq) and 10% NaOH (25 mL, 62 meq) were added. An opaque white gel formed within two minutes. This was stirred at room temperature for 1.5 hours, then filtered and washed three times with water and three times with toluene. The resulting white solid was dried to give 12.3 g (97%) of the product, mp 176°–81° C. The product was relatively insoluble in water, diethyl ether and toluene, but fairly soluble in methanol.

IR(KBr) 3280, 3040, 2920, 2850, 1640, 1605, 1550, 1490, 1440 cm$^{-1}$.

$^1$H-NMR (d6-DMSO) δ8.6 (3H, amide), 8.1 (3H, amide), 7.9 (6H, ortho), 7.5 (9H, meta & para), 3.4 (12H, H-3,4), 2.8 (6H, H-1), 2.4 (6H, H-2); % substitution (NMR)=98%.

| Anal. $C_{36}H_{45}N_7O$ | | | |
|---|---|---|---|
| | C | H | N |
| calcd. | 64.4 | 6.75 | 14.60 |
| found | 64.4 | 6.81 | 14.36. |

D: 1.0 G/NH$_3$-Hexanoyl; N[CH$_2$CH$_2$CONHCH$_2$CH$_2$NHCO—(C$_5$H$_{11}$)]$_3$ The first generation dendrimer from Part A, 3.3 g (28 meq), was dissolved in 25 mL of water in a glass jar. To it was added hexanoyl chloride (3.9 mL, 28 mmole) in 15 mL of toluene and 10% NaOH (11.0 mL, 28 meq). Shaking produced a white gel. The solid was filtered and washed twice with water and with toluene. Drying provided 3.5 g (58%) of the product as a white solid, mp 192°–5° C. The product was relatively insoluble in water, diethyl ether and toluene, but fairly soluble in methanol.

IR(KBr) 3300, 3080, 2930, 2880, 1640, 1550, 1450 cm$^{-1}$.

$^1$H-NMR (d6-DMSO) δ3.1 (12H, H-3,4), 2.5 (6H, H-1), 2.2 (6H, H-2), 2.0 (6H, —CH$_2$CO$_2$—), 1.3 (18H, —C$_3$H$_6$—), 0.8 (9H, CH$_3$); % substitution (NMR)=90%.

E: 1.0 G/NH$_3$-Octanoyl; N[CH$_2$CH$_2$CONHCH$_2$CH$_2$NHCO—(C$_7$H$_{15}$)]$_3$ The first generation dendrimer from Part A, 3.3 g (28 meq), was reacted with octanoyl chloride (4.7 mL, 28 meq) according to the procedure of Part D above. The product was a white solid, 6.2 g (91%), mp 194°–8° C. The product was relatively insoluble in water, diethyl ether and toluene, but fairly soluble in methanol.

F: 1.0 G/NH$_3$-Decanoyl; N[CH$_2$CH$_2$CONHCH$_2$CH$_2$NHCO—(C$_9$H$_{19}$)]$_3$ The first generation dendrimer from Part A, 3.3 g (28 meq), was reacted with decanoyl chloride (5.7 mL, 28 meq) according to the procedure of Part D above. The product was a white gel which held the entire volume of water and toluene. The product was filtered, then washed twice each with water, toluene and acetone. Drying gave the product as a white solid, 6.8 g (90%), mp 195°–201° C. The product was relatively insoluble in water, diethyl ether and toluene, but fairly soluble in methanol.

G: 1.0 G/NH$_3$-Dodecanoyl; N[CH$_2$CH$_2$CONHCH$_2$CH$_2$NHCO—(C$_{11}$H$_{23}$)]$_3$ The first generation dendrimer from Part A, 9.30 g (78 meq), was dissolved in 50 mL of water with 50 mL of toluene in a mechanically stirred three-neck flask. To it was added dropwise dodecanoyl chloride (18.0 mL, 78 meq) in 30 mL of toluene. During this addition 10% of NaOH (31.1 mL, 80 meq) was also added.

The white gelatinous product was stirred for an additional 1.5 hours then filtered and rinsed twice each with toluene, water and methanol. The resulting white solid (approx. 180 g) contained large amounts of solvent. Drying provided 21.2 g (90%) of a white powder, mp 196°–201° C. The product was relatively insoluble in water, diethyl ether, methanol and toluene.

IR(KBr) 3300, 3090, 2920, 2860, 1640, 1560, 1460 cm$^{-1}$.

| Anal. $C_{51}H_{99}N_7O_6$ | | | |
|---|---|---|---|
| | C | H | N |
| calcd. | 67.6 | 11.0 | 10.8 |
| found | 66.7 | 10.9 | 9.7. |

H: 1.0 G/NH$_3$-Octadecanoyl; N[CH$_2$CH$_2$CONHCH$_2$CH$_2$NHCO—(C$_{17}$H$_{35}$)]$_3$ The first generation dendrimer from Part A, 10.1 g (84.3 meq), was dissolved in 100 mL of water and added to a 500 mL separatory funnel containing stearoyl chloride (30.3 g, 100 mmole) in 150 mL of toluene. When shaken, the mixture became warm and a thick gel formed. To the gel was added 10% of NaOH (80 mL, 200 mmole) along with an additional 100 mL of water.

After twenty minutes the creamy white material was filtered and washed with water and with acetone, and dried to give 32.4 g (99%) of the product as a white powder, mp 190°–198° C. The product was relatively insoluble in water, diethyl ether, methanol and toluene.

EXAMPLE 6

Phenyl Tetraamine; N[CH$_2$CH$_2$NHCO—(C$_6$H$_5$)]$_3$

The branched tetraamine, N(CH$_2$CH$_2$NH$_2$)$_3$, 2.0 g, (41 meq) was dissolved in 20 mL of water and placed in a 125 mL separatory funnel with benzoyl chloride (4.8 mL, 41 meq) in 20 mL of toluene. To the mixture was added 10% NaOH (16.5 mL, 41 meq) and the mixture was shaken for 15 minutes.

A ball of oily white solid precipitated. This solid was washed twice with water and with toluene, then dried to give 6.4 g (102%) of the product as a white powder, mp 144°–9° C. The product was relatively insoluble in water, diethyl ether and toluene, but fairly soluble in methanol.

IR(KBr) 3360, 3300, 3080, 2930, 1640, 1610, 1550, 1480, 1460 cm$^{-1}$.

$^1$H-NMR (d6-DMSO) δ8.3 (3H, amide), 7.7 (6H, ortho), 7.3 (9H, meta+para), 3.3 (6H-1), 2.7 (6H, H-2); % substitution (NMR)=104%.

| Anal. $C_{27}H_{30}N_4O_3$ | | | |
|---|---|---|---|
| | C | H | N |
| calcd. | 70.7 | 6.59 | 12.2 |
| found | 70.9 | 6.52 | 11.8. |

EXAMPLE 7

Derivatives of 1st Generation Dense Star Dendrimer from Ethylene Diamine (1.0 G/EDA)

A: 1.0 G/EDA-Benzoyl; $(CH_2N)_2$ [$CH_2CH_2CONHCH_2CH_2NHCO$—$(C_6H_5)]_4$

The first generation amidoamine dendrimer from of ethylenediamine (EDA; 1.0 G/EDA), 3.1 g (24 meq), was dissolved in 20 mL of water with 10% of NaOH (10 mL, 25 meq). To this mixture was added benzoyl chloride (2.8 mL, 24 meq) in 30 mL of toluene. The mixture was shaken and a white precipitate formed.

The reaction mixture stayed as two phases with only a slight amount of gelation. The majority of the product formed a waxy ball. After two hours the solid was filtered, washed twice each with water and toluene, then dried. The product was a white powder, 4.95 g (88%), mp 190°–6° C. The product was relatively insoluble in water, diethyl ether and toluene, but fairly soluble in methanol.

$^1$H-NMR (d6-DMSO) δ8.5 (4H, amide), 8.1 (4H, amide), 7.9 (8H, ortho), 7.5 (12H, meta & para), 3.4 (16H, H-3,4), 2.8–2.3 (20H, H-1,2+$NCH_2CH_2N$); % substitution (NMR)= 104%.

B: 1.0 G/EDA-Dodecanoyl; $(CH_2N)_2$ [$CH_2CH_2CONHCH_2CH_2NHCO$—$(C_{11}H_{23})]_4$ The 1.0 G/EDA dendrimer, 3.1 g (24 meq), prepared in Part A above, was dissolved in 20 mL of water and 2.5M of NaOH (10 mL, 25 meq) and reacted with dodecanoyl chloride (5.5 mL, 24 meq) in 30 mL of toluene. Shaking provided a dense creamy white gel which solidified within fifteen minutes.

After two hours the solid was filtered, washed with excess water and toluene, then with acetone. Drying gave 5.65 g (76.%) of the product as a white powder, mp 195°–202° C. The product was relatively insoluble in water, diethyl ether, methanol and toluene.

IR(KBr) 3300, 3090, 2920, 2860, 1640, 1560, 1460 cm$^{-1}$.

| Anal. $C_{70}H_{136}N_{10}O_8$ | | | |
|---|---|---|---|
| | C | H | N |
| calcd. | 67.5 | 11.0 | 11.2 |
| found | 67.8 | 11.1 | 10.2. |

EXAMPLE 8

Benzoyl Derivative of 3rd Generation Dense Star Dendrimer from Ethylene Diamine (3.0 GDA-Benzol)

The 3.0 G dendrimer from an EDA core, 2.50 g (12.3 meq), was dissolved in 40 mL of water and placed in a mechanically stirred 500 mL round bottom flask along with 25 mL of toluene. To this mixture was added 10% of NaOH (4.9 mL, 12.3 meq), then benzoyl chloride (1.43 mL, 12.3 meq) in 25 mL of toluene.

The mixture was stirred and an oily white solid precipitated. The liquid was decanted and the solid was taken up in methanol, then precipitated with ether and dried to give 3.43 g (90%) of the product as a white solid, m.p. 120°–5° C. (flows), 198°–203° C. (clears). The product was relatively insoluble in water, diethyl ether and toluene, but fairly soluble in methanol.

IR(KBr) 3400, 3300, 3090, 2920, 2850, 1650, 1610, 1550, 1490, 1440 cm$^{-1}$.

$^1$H-NMR (d6-DMSO) δ8.5 (amide), 8.0 (amide), 7.7 (32H, ortho), 7.4 (48H, meta+para), 3.3 (88H, H-3,3'), 2.7 (80H, H-1,1'), 2.2 (56H, H-2); % substitution (NMR)= 104%.

EXAMPLE 9

Derivative of 4th Generation Dense Star Dendrimer from Ethylene Diamine (4.0 G/EDA)

A: 4.0 G/EDA-Butyryl; $(NCH_2CH_2N)$~~~~~~~$(NHCO$—$C_3H_7)]_{32}$

The dense star dendrimer, $(NCH_2CH_2N)$~~~~~~~$(NH_2)_{32}$, (4.0 G/EDA), 3.06 g (14.2 meq), in 20 mL of water was reacted with butyryl chloride (1.6 mL, 15.2 meq) in 25 mL toluene and 10% of NaOH (7.1 mL, 25% excess). The product did not precipitate but was isolated by evaporation of the aqueous phase. It was purified by dissolving it twice in ethanol, filtering, and precipitating with ether. Drying provided 2.67 g (70%) of the product as a white solid, mp 112°–7° C. (flows), 212°–217° C. (clears). The product was relatively insoluble in diethyl ether and toluene, but fairly soluble in water and methanol.

IR(KBr) 3290, 3080, 2950, 2880, 2820, 1650, 1550, 1460, 1440 cm$^{-1}$.

$^1$H-NMR (d6-DMSO) δ8.0 (amide), 3.2 (368H, H-3,3'), 2.6 (352H, H-1,1'), 2.2 (240H, H-2), 2.1 (128H, —$CH_2CO_2$), 1.5 (128H, —$CH_2$—), 0.9 (192H, $CH_3$); % substitution (NMR)=93%.

B: 4.0 G/EDA-Benzoyl; $(NCH_2CH_2N)$~~~~~~~[(NHCO—$C_6H_5$)]$_{32}$

The dense star dendrimer, $(NCH_2CH_2N)$~~~~~~~$(NH_2)_{32}$, (4.0 G/EDA), 3.06 g (14.2 meq), in 20 mL of water was reacted with benzoyl chloride (1.82 mL, 15.6 meq) in 25 mL of toluene and 10% of NaOH (7.1 mL, 25% excess). The product was an oily ball and was isolated as with $(CH_2N)_2$ [$CH_2CH_2CONHCH_2CH_2NHCO$—$(C_6H_5)]_4$ described in Example 8. Drying provided 4.16 g (92%) of the product as a fluffy crystalline white solid, mp 120°–7° C. (flows), 48°–155° C. (clears). The product was relatively insoluble in water, diethyl ether and toluene, but fairly soluble in methanol.

$^1$H-NMR (d6-DMSO) δ8.5 (32H, amide), 8.0 (60H, amide), 7.8 (64H, ortho), 7.5 (96H, meta & para), 3.3 (184H, H-3,3'), 2.8 (176H, H-1,1'), 2.2 (120H, H-2); % substitution (NMR)=103%.

| Anal. $C_{526}H_{736}N_{122}O_{92}$ | | | |
|---|---|---|---|
| | C | H | N |
| calcd. | 61.7 | 7.24 | 16.7 |
| found | 61.4 | 7.12 | 15.6. |

C: 4.0 G/EDA-Octanoyl; $(NCH_2CH_2N)$~~~~~~~[(NHCO—$C_7H_{15}$)]$_{32}$

The dense star dendrimer (NCH$_2$CH$_2$N)~~~~~~(NH$_2$)$_{32}$, (4.0 G/EDA), 3.06 g (14.2 meq), was reacted with octanoyl chloride (1.82 mL, 15.6 meq) as described for Part B above. The product was a white solid, 3.37 g (70%), mp 150°–5° C. (flows), >225° C. (clears). The product was relatively insoluble in water, diethyl ether and toluene, but fairly soluble in methanol.

D: 4.0 G/EDA-Dodecanol; (NCH$_2$CH$_2$N)~~~~~~[(NHCO—(C$_n$H$_{23}$)]$_{32}$

The dense star dendrimer (NCH$_2$CH$_2$N)~~~~~~(NH$_2$)$_{32}$, (4.0 G/EDA), 3.06 g (14.2 meq), was reacted with dodecanoyl chloride (3.61 mL, 15.6 meq) as described for Part B above. The product was a stiff white paste which held all of the reaction solvent. This material was filtered, washed twice each with water, toluene and acetone, then dried to give 4.35 g (77%) of the product as a white powder, mp 170°–5° C. (flows), 201°–7° C. (clears). The product was relatively insoluble in water, methanol, diethyl ether and toluene.

IR(KBr) 3300, 3080, 2910, 2860, 1640, 1560, 1470 cm$^{-1}$.

| Anal. C$_{686}$H$_{1312}$N$_{122}$O$_{92}$ | | | |
|---|---|---|---|
| | C | H | N |
| calcd. | 64.7 | 10.38 | 13.4 |
| found | 65.5 | 10.60 | 11.7 |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A modified dense star polymer having a highly branched interior structure comprised of monomeric units having associated or chelated at least one metal ion and an exterior structure comprised of a different monomeric unit providing a hydrophobic outer shell.

2. The polymer of claim 1 in which the modified dense star polymer is a dendrimer.

3. The polymer of claim 1 in which the highly branched interior structure is comprised of an amine-terminated poly(amidoamine) dendrimer, a hydroxy-terminated poly(ether) dendrimer, an amine-terminated poly(ethyleneimine) dendrimer, or an amine-terminated poly(propyleneimine) dendrimer.

4. The polymer of claim 3 in which the poly(amidoamine), poly(ether) or poly(ethyleneimine) dendrimer is from 2 to 12 generations.

5. The polymer of claim 1 in which the hydrophobic outer shell is comprised of hydrocarbon groups of from 4 to 40 carbon atoms inclusive.

6. The polymer of claim 5 in which the hydrocarbon groups contain of from 4 to 24 carbon atoms inclusive.

7. The polymer of claim 5 in which the hydrocarbon groups include linear alkyl groups having from 4 to 40 carbon atoms optionally substituted independently with hydroxy, with carboxyl, with C$_1$–C$_{10}$ alkyl, with C$_1$–C$_{10}$ alkoxy, with C$_1$–C$_{10}$ alkoxycarbonyl, with phenyl or phenyl substituted with from 1 to 5 groups of C$_1$–C$_5$ alkyl or C$_1$–C$_5$ alkoxy groups, or with phenoxy or phenoxy substituted with C$_1$–C$_5$ alkyl or C$_1$–C$_5$ alkoxy groups.

8. The polymer of claim 7 in which the hydrocarbon groups are hexyl, octadecyl, ethylhexyl, tolyldecyl group, anisyldodecyl group, 3-phenoxy-2-hydroxy-1-propyl, (4-methyl)phenoxy-2-hydroxy-1-propyl, (4-methoxy)phenoxy-2-hydroxy-1-propyl, telechelic polymers, 2-hydroxyalkyl moieties formed from the opening of epoxy moieties, or alkylation of the hydroxy groups from the 2-hydroxyalkyl moieties to provide the alkoxy groups.

9. The polymer of claim 1 wherein the modified dense star polymer is derived from an amine-terminated poly(amidoamine) dendrimer as its highly branched interior structure.

10. The polymer of claim 1 wherein the modified dense star polymer is derived from an hydroxy-terminated poly(ether) dendrimer as its highly branched interior structure.

11. The polymer of claim 1 wherein the modified dense star polymer is derived from an amine-terminated poly(ethyleneimine) dendrimer as its highly branched inferior structure.

12. The polymer of claim 1 wherein the modified dense star polymer is glycidyl phenyl ether modified tenth generation polyamidoamine dendrimer and the metal ion is copper.

13. A polymer blend comprising a modified dense star polymer associated with a metal ion and a polymer matrix.

14. The polymer blend of claim 13 wherein the modified dense star polymer is a modified poly(amidoamine) dense star polymer.

15. The polymer blend of claim 13 wherein the polymer matrix is polystyrene.

16. A process for dispersing a modified dense star polymer containing metal ions into a non-polar polymer matrix which comprises:

(a) intimately contacting the aqueous solution containing metal ions with a solution of a modified dense star polymer, having a highly branched interior structure comprised of monomeric units having the ability to associate or chelate with metal ions and an exterior structure comprised of a different monomeric unit having the ability to provide a hydrophobic outer shell, once introduced into a water-immiscible solvent, (b) (i) optionally separating the organic phase which is usually soluble or miscible with the desired polymer matrix or the monomeric precursor to the polymeric matrix from the aqueous solution, and (ii) intermixing the modified dense star polymer carrying the associated metal ion with the non-polar media either before or after removal of the water-immiscible extraction solvent, and (c) polymerizing the mixture from step (c) when the non-polar media is a monomer.

17. A modified dense star polymer having a highly branched interior structure comprised of hydrophilic monomeric units and an exterior structure comprised of a different monomeric unit providing a hydrophobic outer shell.

18. The polymer of claim 17 in which the hydrophobic outer shell is trimethylacetyl.

19. The polymer of claim 18 in which the branched interior is derived from ammonia.

20. The polymer of claim 17 in which the hydrophobic outer shell is benzoyl.

21. The polymer of claim 20 in which the branched interior is derived from ammonia or ethylene diamine.

22. The polymer of claim 17 in which the hydrophobic outer shell is hexanoyl, octanoyl, decanoyl, dodecanoyl, or octadecanoyl.

23. The polymer of claim 22 in which the branched interior is derived from ammonia or ethylene diamine.

* * * * *